US 8,148,595 B2

United States Patent
Robinson et al.

(10) Patent No.: US 8,148,595 B2
(45) Date of Patent: *Apr. 3, 2012

(54) BREATHABLE INTERFACE SYSTEM FOR TOPICAL REDUCED PRESSURE

(75) Inventors: Timothy Mark Robinson, Basingstoke (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/015,209

(22) Filed: Jan. 27, 2011

(65) Prior Publication Data

US 2011/0125066 A1   May 26, 2011

Related U.S. Application Data

(63) Continuation of application No. 12/069,245, filed on Feb. 8, 2008, now Pat. No. 7,880,050.

(60) Provisional application No. 60/900,463, filed on Feb. 9, 2007.

(51) Int. Cl.
 *A61F 13/00* (2006.01)
 *A61F 13/15* (2006.01)
 *A61M 27/00* (2006.01)

(52) U.S. Cl. .......... 602/44; 602/43; 602/46; 604/385.1; 604/543

(58) Field of Classification Search .............. 602/41–46; 604/304–307, 317, 313, 543, 385.01, 327, 604/328, 540, 541, 367
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,376,868 A | 4/1968 | Mondiadis |

(Continued)

FOREIGN PATENT DOCUMENTS

AU   550575 A1   8/1982

(Continued)

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksa, U.S.S.R. 1986);pp. 94-96 (copy and certified translation).

(Continued)

*Primary Examiner* — Patricia Bianco
*Assistant Examiner* — Ophelia Hawthorne

(57) ABSTRACT

A reduced pressure tissue treatment system includes an applicator having an aperture, a first pad section, and a second pad section substantially covering the aperture and positioned substantially adjacent the first pad section. A fabric layer is located at least partially between the second pad section and the drape, and the fabric layer includes a woven or non-woven fabric made from a fiber material. A drape substantially covers the first pad section, the second pad section, the fabric layer, and the applicator. A reduced pressure source is in fluid communication with at least one of the first pad section and the fabric layer for providing reduced pressure to the aperture.

22 Claims, 4 Drawing Sheets

U.S. PATENT DOCUMENTS

| | | |
|---|---|---|
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,742,952 A | 7/1973 | Magers et al. |
| 3,763,857 A | 10/1973 | Schrading |
| 3,774,611 A | 11/1973 | Tussey et al. |
| 3,779,243 A | 12/1973 | Tussey et al. |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,141,361 A | 2/1979 | Snyder |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,529,402 A | 7/1985 | Weilbacher et al. |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,652 A | 5/1987 | Weilbacher |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,841,962 A | 6/1989 | Berg et al. |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,981,474 A | 1/1991 | Bopp et al. |
| 4,985,019 A | 1/1991 | Michelson |
| 5,000,164 A | 3/1991 | Cooper |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,112,323 A | 5/1992 | Winkler et al. |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,215,539 A | 6/1993 | Schoolman |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,329 A | 8/1994 | Croquevielle |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,449,379 A | 9/1995 | Hadtke |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,688,225 A | 11/1997 | Walker |
| 5,784,811 A | 7/1998 | Mauch |
| 5,809,665 A | 9/1998 | Suenagal |
| 5,913,838 A | 6/1999 | Reilly |
| 6,071,267 A | 6/2000 | Zamierowski |
| 6,129,692 A | 10/2000 | Mathis |
| 6,135,116 A | 10/2000 | Vogel et al. |
| 6,174,306 B1 | 1/2001 | Fleischmann |
| 6,178,662 B1 | 1/2001 | Legatzke |
| 6,241,747 B1 | 6/2001 | Ruff |
| 6,287,316 B1 | 9/2001 | Agarwal et al. |
| 6,290,685 B1 | 9/2001 | Insley et al. |
| 6,345,623 B1 | 2/2002 | Heaton et al. |
| 6,360,457 B1 | 3/2002 | Qui et al. |
| 6,361,512 B1 | 3/2002 | Mackay et al. |
| 6,425,194 B1 | 7/2002 | Brie |
| 6,471,685 B1 | 10/2002 | Johnson |
| 6,488,643 B1 | 12/2002 | Tumey et al. |
| 6,493,568 B1 | 12/2002 | Bell et al. |
| 6,553,998 B2 | 4/2003 | Heaton et al. |
| 6,626,891 B2 | 9/2003 | Ohmstede |
| 6,631,568 B2 | 10/2003 | Howlett et al. |
| 6,663,610 B1 | 12/2003 | Thompson et al. |
| 6,685,681 B2 | 2/2004 | Lockwood et al. |
| 6,695,824 B2 | 2/2004 | Howard et al. |
| 6,736,787 B1 | 5/2004 | McEwen et al. |
| 6,752,794 B2 | 6/2004 | Lockwood et al. |
| 6,814,079 B2 | 11/2004 | Heaton et al. |
| 6,855,135 B2 | 2/2005 | Lockwood et al. |
| 6,979,324 B2 | 12/2005 | Bybordi et al. |
| 7,070,584 B2 | 7/2006 | Johnson et al. |
| 7,207,977 B2 | 4/2007 | Thompson et al. |
| 7,279,612 B1 | 10/2007 | Heaton et al. |
| 7,282,038 B2 | 10/2007 | Gillis et al. |
| 7,880,050 B2 | 2/2011 | Robinson et al. |
| 2001/0000262 A1 | 4/2001 | McEwen et al. |
| 2001/0031943 A1 | 10/2001 | Urie |
| 2001/0043943 A1 | 11/2001 | Coffey |
| 2002/0017304 A1 | 2/2002 | Heaton et al. |
| 2002/0065494 A1 | 5/2002 | Lockwood et al. |
| 2002/0077661 A1 | 6/2002 | Saadat |
| 2002/0082567 A1 | 6/2002 | Lockwood et al. |
| 2002/0115951 A1 | 8/2002 | Norstrem et al. |
| 2002/0115952 A1 | 8/2002 | Johnson et al. |
| 2002/0120185 A1 | 8/2002 | Johnson |
| 2002/0143286 A1 | 10/2002 | Tumey |
| 2002/0150720 A1 | 10/2002 | Howard et al. |
| 2002/0178499 A1 | 12/2002 | Augustine et al. |
| 2002/0198504 A1 | 12/2002 | Risk, Jr. et al. |
| 2003/0050594 A1 | 3/2003 | Zamierowski |
| 2003/0061733 A1 | 4/2003 | Karsten |
| 2003/0125649 A1 | 7/2003 | McIntosh et al. |
| 2003/0176828 A1 | 9/2003 | Buckman et al. |
| 2003/0216672 A1 | 11/2003 | Rastegar et al. |
| 2004/0030304 A1 | 2/2004 | Hunt et al. |
| 2004/0064132 A1 | 4/2004 | Boehringer et al. |
| 2005/0004534 A1 | 1/2005 | Lockwood et al. |
| 2005/0020955 A1 | 1/2005 | Sanders et al. |
| 2005/0027218 A1 | 2/2005 | Filtvedt et al. |
| 2005/0070858 A1 | 3/2005 | Lockwood et al. |
| 2005/0101940 A1 | 5/2005 | Radl et al. |

| | | | |
|---|---|---|---|
| 2005/0137539 | A1 | 6/2005 | Biggie et al. |
| 2005/0228329 | A1 | 10/2005 | Boehringer et al. |
| 2005/0261642 | A1 | 11/2005 | Weston |
| 2005/0261643 | A1 | 11/2005 | Bybordi et al. |
| 2006/0100556 | A1 | 5/2006 | Hargens et al. |
| 2006/0100586 | A1 | 5/2006 | Karpowicz et al. |
| 2006/0149171 | A1 | 7/2006 | Vogel et al. |
| 2006/0155260 | A1 | 7/2006 | Blott et al. |
| 2006/0189909 | A1 | 8/2006 | Hurley et al. |
| 2006/0189910 | A1 | 8/2006 | Johnson et al. |
| 2006/0287621 | A1 | 12/2006 | Atkinson et al. |
| 2007/0027414 | A1 | 2/2007 | Hoffman et al. |
| 2007/0060848 | A1 | 3/2007 | Erdmann |
| 2007/0124959 | A1 | 6/2007 | Meffan |
| 2007/0167884 | A1 | 7/2007 | Mangrum et al. |
| 2007/0185426 | A1 | 8/2007 | Ambrosio et al. |
| 2007/0218101 | A1 | 9/2007 | Johnson et al. |
| 2007/0225663 | A1 | 9/2007 | Watt et al. |
| 2007/0265585 | A1 | 11/2007 | Joshi et al. |
| 2007/0265586 | A1 | 11/2007 | Joshi et al. |
| 2008/0047164 | A1 | 2/2008 | Vindriis |
| 2008/0066343 | A1 | 3/2008 | Sanabria-Hernandez |
| 2008/0071234 | A1 | 3/2008 | Kelch et al. |

FOREIGN PATENT DOCUMENTS

| | | |
|---|---|---|
| AU | 745271 | 4/1999 |
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| DE | 19844355 A1 | 4/2000 |
| DE | 10 2004 055 702 B3 | 11/2005 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| EP | 1872763 A1 | 1/2008 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| GB | 2415908 A | 1/2006 |
| JP | 4129536 | 4/1992 |
| JP | 2003-532504 | 11/2003 |
| SG | 71559 | 4/2002 |
| WO | WO 80/02182 | 10/1980 |
| WO | WO 87/04626 | 8/1987 |
| WO | WO 88/01499 A1 | 3/1988 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 96/06559 A1 | 3/1996 |
| WO | WO 97/18007 | 5/1997 |
| WO | WO 99/13793 | 3/1999 |
| WO | WO 00/59424 A1 | 10/2000 |
| WO | WO 00/64394 A1 | 11/2000 |
| WO | WO 01/85248 A1 | 11/2001 |
| WO | WO 01/89431 A1 | 11/2001 |
| WO | WO 03/057307 A1 | 7/2003 |
| WO | WO 03/099188 A1 | 12/2003 |
| WO | WO 2004/018020 A1 | 3/2004 |
| WO | WO 2005/123170 | 12/2005 |
| WO | WO 2006/087021 A1 | 8/2006 |
| WO | WO 2007/092397 A2 | 8/2007 |
| WO | WO 2007/133618 A2 | 11/2007 |
| WO | WO 2008/036361 A2 | 3/2008 |
| WO | WO 2008/057600 A2 | 5/2008 |
| WO | WO 2008/100440 A1 | 8/2008 |
| WO | WO 2008/100446 A2 | 8/2008 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written, Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumas, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter T.E. Tintle and M. Chariker, Managing Draining Wounds and Fistulae: "New and Established Methods," Chronic Wound Care, edited by D. Krasner (Health Management Publications, Inc., King of Prussia, PA 1990), pp. 240-246.

G. Živadinović, V. Dukić, Ž. Maksimović, D. Radak, and P. Peška, "Vacuum Therapy in the Treatment of Peripheral Blood Vessels," *Timok Medical Journal* 11 (1986), pp. 161-164 (copy and certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians (Jul. 2007).

Merriam OnLine definitions—"occlusive", "occlude" and "occluding" (unknown date).

Arcand, "Negative Pressure Wound Therapy and its Application to Othopaedics. Part II: Clinical Application", Osteo Trauma Care 2006; 14-254-258.

Culliford, "A Novel Technique for Vacuum Assisted Closure Device Application in Noncontiguous Wounds", Journal of Plastic, Reconstructive & Aesthetic Surgery 2006.

Armstrong, "Plantar Pressure Changes Using a Novel Negative Pressure Wound Therapy Technique", Journal of the American Podiatric Medical Association, Sep./Oct. 2004, vol. 94. No. 5, pp. 456-460.

"Guidelines for Managing Pressure Ulcers with Negative Pressure Wound Therapy", a Supplement of Advances in Skin & Wound Care, vol. 17, Suppl. 2, Nov./Dec. 2004.

Venturi, "Mechanisms and Clinical Applications of the Vacuum-Assisted Closure (VAC) Device", Am J Clin Dermatol 2005: 6(3): 185-194.

Lavery, Lawrence, et al: "Emerging Concepts with VAC Therapy"; vol. 20, Publication date Jul. 1, 2007, Issue No. 7.

NPD 1000 Negative Pressure Wound Therapy System, Kalypto Medical, pp. 1-4.

International Search Report and Written Opinion date mailed Feb. 19, 2009; PCT Application No. PCT/US2008/088635.

Non-Final Office Action dated Dec. 16, 2005 for U.S. Appl. No. 10/895,700.

Response filed Jun. 15, 2006 for U.S. Appl. No. 10/895,700.

Notice of Non-Compliant Amendment dated Sep. 5, 2006 for U.S. Appl. No. 10/895,700.

Reply to Notice of Non-Compliant Amendment filed Oct. 5, 2006 for U.S. Appl. No. 10/895,700.

Official Action Response to Amendment dated Dec. 22, 2006 for U.S. Appl. No. 10/895,700.

Response filed Jan. 19, 2007 for U.S. Appl. No. 10/895,700.

Supplemental Amendment filed Mar. 21, 2007 for U.S. Appl. No. 10/895,700.

Final Office Action dated Jun. 11, 2007 for U.S. Appl. No. 10/895,700.

Response filed Sep. 11, 2007 for U.S. Appl. No. 10/895,700.

Notice of Non-Compliant Amendment dated Nov. 29, 2007 for U.S. Appl. No. 10/895,700.

Response filed Jan. 23, 2008 for U.S. Appl. No. 10/895,700.

Non-Final Office Action dated Mar. 18, 2008 for U.S. Appl. No. 10/895,700.

Response filed Jun. 17, 2008 for U.S. Appl. No. 10/895,700.

Final Office Action dated Sep. 19, 2008 for U.S. Appl. No. 10/895,700.

RCE/Amendment filed Jan. 21, 2009 for U.S. Appl. No. 10/895,700.

Examiner Interview Summary date mailed Mar. 2, 2009 for U.S. Appl. No. 10/895,700.

Supplemental Response/Amendment filed Mar. 25, 2009 for U.S. Appl. No. 10/895,700.

Non-Final Rejection date mailed May 27, 2009 for U.S. Appl. No. 10/895,700.

Examiner Interview Summary date mailed Sep. 4, 2009 for U.S. Appl. No. 10/895,700.

Amendment filed Oct. 27, 2009 for U.S. Appl. No. 10/895,700.

Final Rejection date mailed Mar. 15, 2010 for U.S. Appl. No. 10/895,700.

Response filed May 14, 2010 for U.S. Appl. No. 10/895,700.

Advisory Action date mailed May 20, 2010 for U.S. Appl. No. 10/895,700.

Notice of Appeal filed Jun. 14, 2010 for U.S. Appl. No. 10/895,700.

Appeal Brief filed Jul. 13, 2010 for U.S. Appl. No. 10/895,700.

Examiner's Answer to Appeal Brief Oct. 13, 2010 for U.S. Appl. No. 10/895,700.

Request for Oral Hearing Reply Brief Dec. 6, 2010—(on Appeal—Appeal No. 2011-004124) for U.S. Appl. No. 10/895,700.

Non-Final Rejection date mailed Apr. 27, 2010 for U.S. Appl. No. 12/069,245.

Response filed Jul. 19, 2010 for U.S. Appl. No. 12/069,245.

Notice of Allowance date mailed Oct. 1, 2010 for U.S. Appl. No. 12/069,245.

Restriction Requirement dated Feb. 25, 2010 for U.S. Appl. No. 12/006,566.

Response filed Mar. 25, 2010 for U.S. Appl. No. 12/006,566.

Non-Final Office Action date mailed May 27, 2010 for U.S. Appl. No. 12/006,566.

Response filed Aug. 26, 2010 for U.S. Appl. No. 12/006,566.

Final Office Action date mailed Nov. 9, 2010 for U.S. Appl. No. 12/006,566.

Interview Summary date mailed Jan. 7, 2011 for U.S. Appl. No. 12/006,566.

Response filed Jan. 10, 2011 for U.S. Appl. No. 12/006,566.

Advisory Action date mailed Jan. 21, 2011 for U.S. Apppl. No. 12/006,566.

RCE/Response filed Feb. 8, 2011 for U.S. Appl. No. 12/006,566.

Non-Final Office Action date mailed Oct. 18, 2011 for U.S. Appl. No. 12/403,296.

Response filed Nov. 15, 2011 for U.S. Appl. No. 12/403,296.

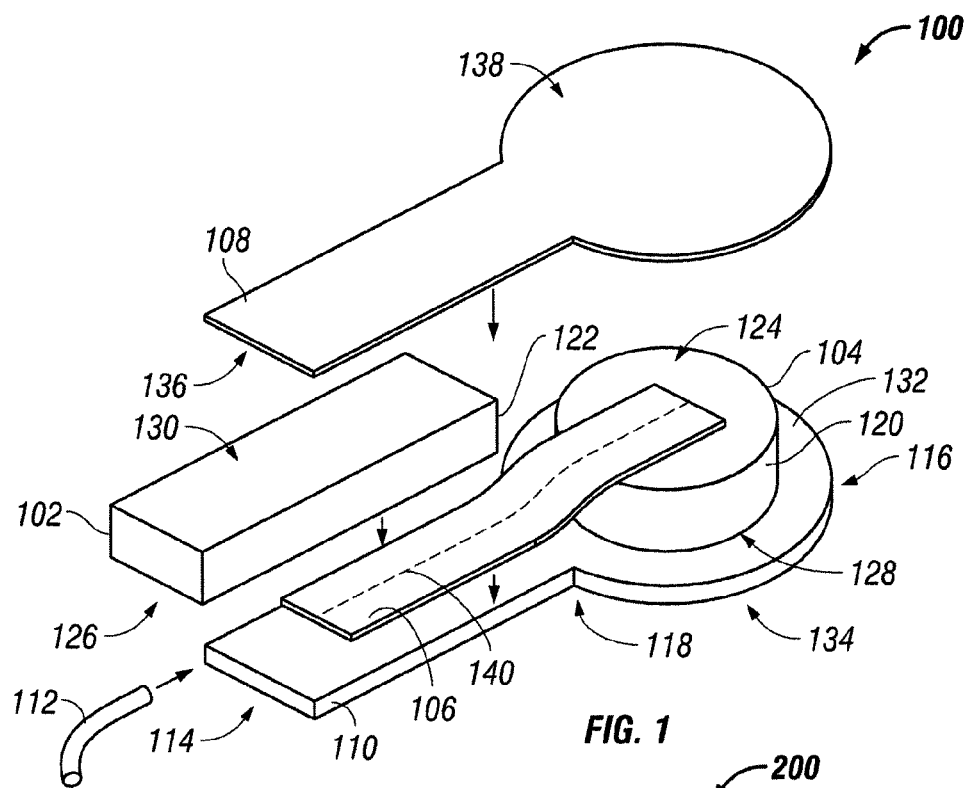
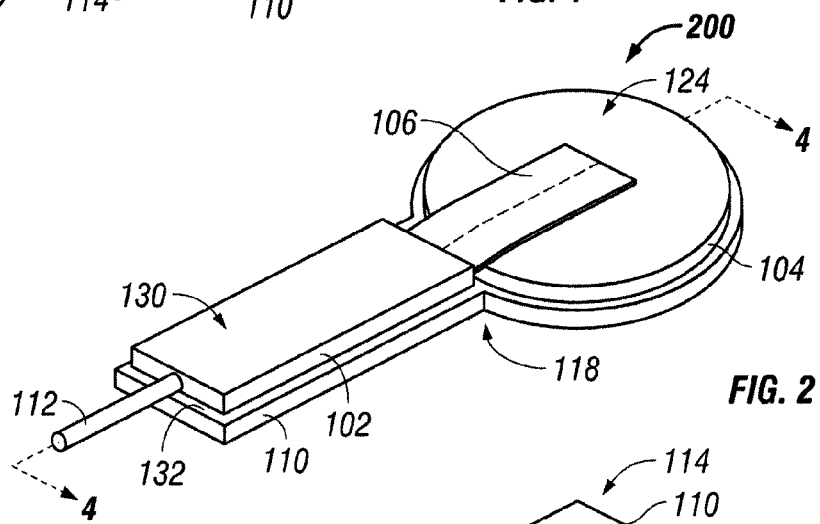
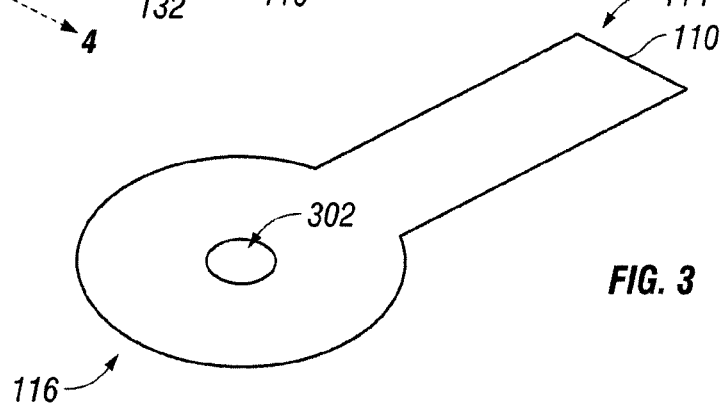
FIG. 1
FIG. 2
FIG. 3

BREATHABLE INTERFACE SYSTEM FOR TOPICAL REDUCED PRESSURE

CROSS-REFERENCE TO RELATED APPLICATIONS

This application is a continuation of U.S. patent application Ser. No. 12/069,245, filed Feb. 8, 2008, now U.S. Pat. No. 7,880,050, which claims the benefit of U.S. Provisional Application No. 60/900,463, filed Feb. 9, 2007, both of which are hereby incorporated by reference.

BACKGROUND OF THE INVENTION

1. Field of the Invention

The present application relates generally to systems and methods for providing reduced pressure tissue treatment to open wounds and other tissue sites. More particularly, the present application relates to a breathable interface systems for topical reduced pressure.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds and tissue sites. This treatment (frequently referred to in the medical community as "negative pressure wound therapy," "reduced pressure therapy," or "vacuum therapy") provides a number of benefits, including faster healing, and increased formulation of granulation tissue.

Reduced pressure tissue treatment has recently been popularized by Kinetic Concepts, Inc. of San Antonio, Tex., through its commercially available VAC reduced pressure tissue treatment systems product line. In general, such reduced pressure tissue treatment systems comprise a pad-based dressing, which is applied to the tissue and is sometimes referred to as the "tissue interface" or the "wound interface."

Current dressings, however, have several disadvantages. They are difficult to apply to small wounds, and often lead to maceration of the wound periphery. Traditionally, dressings have been rather cumbersome, limiting many patient activities. Simply sitting on or rolling onto a dressing may cause significant patient discomfort. Moreover, these actions may compress the dressing and interfere with the application of reduced pressure to a manifold at the tissue site.

SUMMARY

The problems presented with these conventional dressings are solved by an improved breathable interface system for topical reduced pressure. In one illustrative embodiment, a reduced pressure tissue treatment system is provided and includes an applicator having an aperture, a first pad section, and a second pad section. The second pad section substantially covers the aperture and is positioned substantially adjacent the first pad section. A fabric layer is located at least partially between the second pad section and the drape, and the fabric layer includes a woven or non-woven fabric made from a fiber material. A drape substantially covers the first pad section, the second pad section, the fabric layer, and the applicator. A reduced pressure source is in fluid communication with at least one of the first pad section and the fabric layer for providing reduced pressure to the aperture.

In another illustrative embodiment, a reduced pressure tissue treatment system includes an applicator having an aperture, a first pad section, and a second pad section substantially covering the aperture and positioned substantially adjacent to the first pad section. A fabric layer is located at least partially between the first pad section and the applicator, and the fabric layer further is located at least partially between the second pad section and the applicator. A drape substantially covers the first pad section, the second pad section, the fabric layer, and the applicator. A reduced pressure source is in fluid communication with at least one of the first pad section and the fabric layer for providing reduced pressure to the aperture.

In yet another illustrative embodiment, a reduced pressure tissue treatment system includes an applicator having an aperture, a first pad section, and a second pad section substantially covering the aperture and positioned substantially adjacent to the first pad section. A fabric layer is located at least partially between the first pad section and the drape, and the fabric layer further is located at least partially between the second pad section and the drape. A drape substantially covers the first pad section, the second pad section, the fabric layer, and the applicator. A reduced pressure source is in fluid communication with at least one of the first pad section and the fabric layer for providing reduced pressure to the aperture.

Other objects, features, and advantages of the illustrative embodiments will become apparent with reference to the drawings and the detailed description that follow.

BRIEF DESCRIPTION OF THE DRAWINGS

FIG. 1 is an exploded view of the breathable interface system according to an illustrative embodiment of the invention;

FIG. 2 is a perspective view of the breathable interface system without a drape according to an illustrative embodiment of the invention;

FIG. 3 is a bottom view of an applicator of a breathable interface system of FIGS. 1 and 2 according to an illustrative embodiment of the invention;

DETAILED DESCRIPTION OF A PREFERRED EMBODIMENT

Figure 4:
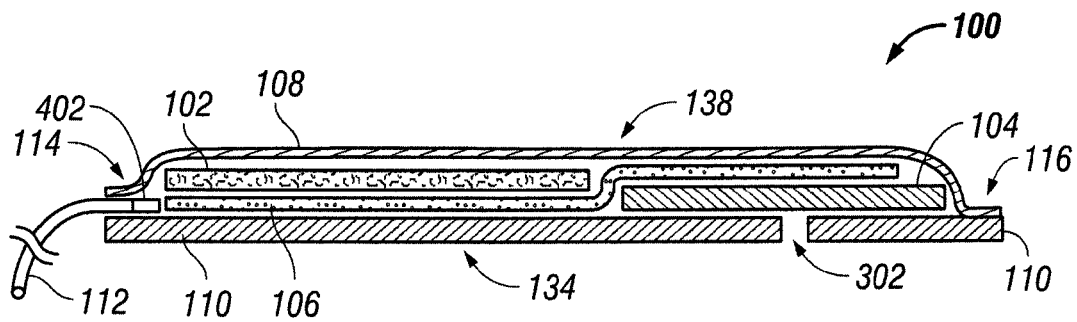
FIG. 4 is cross-sectional view of the breathable interface system along lines 4-4 of FIG. 2 according to an illustrative embodiment of the invention.

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical, structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure of tissue at the tissue site. Although the terms "vacuum" and "negative pressure" may be used to describe the pressure applied to the tissue site, the actual pressure applied to the tissue site may be significantly less than the pressure normally associated with a complete vacuum. Reduced pressure may initially generate fluid flow in the tube in the area of the tissue site. As the hydrostatic pressure around the tissue site approaches the desired reduced pressure, the flow may subside, and the reduced pressure is then maintained. Unless otherwise indicated, values of pressure stated herein are gauge pressures.

The term "tissue site" as used herein refers to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

Referring to FIGS. 1-3, an illustrative embodiment of a breathable interface system 100 is shown. In this embodiment, the breathable interface system 100 includes a first pad section 102, a second pad section 104, and a fabric layer 106, all positioned between a drape 108 and an applicator 110. The breathable interface system 100 generally has one end 116 that is located substantially adjacent to or over a tissue site and another end 114 that is located distally away from end 116, in one example. Nearer to end 114, the fabric layer 106 may be positioned or located at least partially between the applicator 110 and the first pad section 102. Nearer to end 116, the fabric layer 106 may be positioned or located at least partially between the second pad section 104 and the drape 108. The fabric layer 106 extends along a portion of a top surface 124 of the second pad section 104 between the second pad section 104 and the drape 108. Once the fabric layer 106 reaches a side 120 of the second pad section 104 it transitions near the area 118 between the side 120 of the second pad section 104 and the side 122 of the first pad section 102 to extend along a portion of the bottom surface 126 of the first pad section 102 between the first pad section 102 and the applicator 110.

FIG. 2 is an illustrative embodiment of a breathable interface system 200 without the drape 108 placed on top of the first pad section 102, second pad section 104, and fabric layer 106 for illustration purposes. The fabric layer 106 can be seen extending over the top surface 124 of the second pad section 104 and beneath the bottom surface 126 of the first pad section 102. FIG. 3 is an illustrative embodiment of the applicator 110 including an aperture 302 that extends through the applicator 110 substantially near the end 116 of the applicator 110. The aperture 302 preferably is located near a tissue site to enable fluid to flow from the tissue site to the first pad section 102, second pad section 104, fabric layer 106, and reduced pressure conduit 112 of the breathable interface systems herein described.

Figure 5:
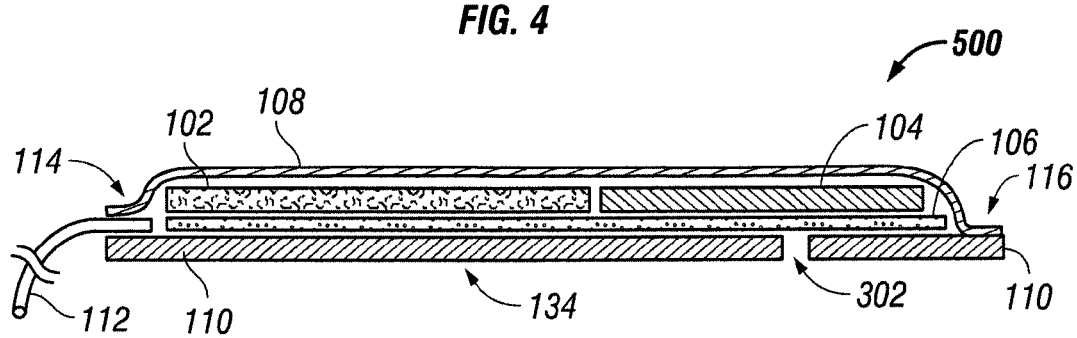
FIG. 5 is cross-sectional view of the breathable interface system according to another illustrative embodiment of the invention.
Figure 6:
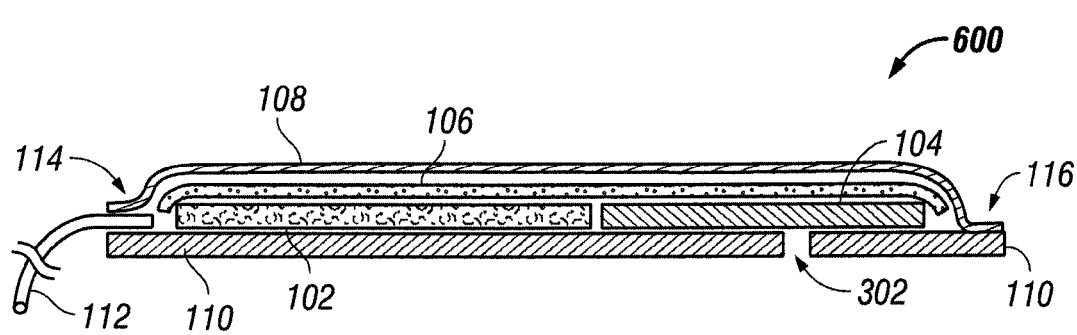
FIG. 6 is cross-sectional view of the breathable interface system according to another illustrative embodiment of the invention.

In an illustrative embodiment, any hydrogel or bonding agent may be applied to the aperture 302 and the applicator 110 for sealing or contact purposes with a tissue site. The second pad section 104 is generally positioned to substantially cover the aperture 302, between the drape 108 and the applicator 110 as shown in FIGS. 4 and 6. In FIG. 5, the aperture 302 may be substantially covered by the fabric layer 106 as described herein. The size of the aperture 302 may vary to accommodate larger wounds, but in one embodiment, a size of about 10 to about 20 mm is advantageous for small wounds.

Referring to FIG. 4, an illustrative embodiment of the breathable interface system 100 is shown. The aperture 302 is shown disposed through the applicator 110. In addition, the breathable interface system 100 may further include an interface 402 that facilitates fluid communication between the first pad section 102 and/or fabric layer 106 and the reduced pressure conduit 112. Referring to FIG. 5, another illustrative embodiment of the breathable interface system 500 is shown. The breathable interface system 500 may include a different arrangement of the first pad section 102, second pad section 104, and fabric layer 106 between the drape 108 and the applicator 110. In this illustrative embodiment, the fabric layer 106 is located between the bottom surface 126 of the first pad section 102 and the bottom surface 128 of the second pad section 104 and the top surface 132 of the applicator 110. The first pad section 102 and second pad section 104 are located or positioned on top of the fabric layer 106. In this illustrative embodiment, the fabric layer 106 substantially covers the aperture 302. Referring to FIG. 6, yet another illustrative embodiment of the breathable interface system 600 is shown. In this illustrative embodiment, the fabric layer 106 is located between the top surface 124 of the second pad section 104 and the top surface 130 of the first pad section 102 and the bottom surface 136 of the drape 108.

In any of the breathable interface systems 100, 200, 500, and 600, the reduced pressure conduit 112 may be located in direct contact with the first pad section 102 and/or the fabric layer 106. The reduced pressure conduit 112 may be placed in direct contact with the first pad section 102 or the fabric layer 106 by directly inserting it into either of the first pad section 102 or the fabric layer 106 near the end 114 of the breathable interface system 100. In another illustrative embodiment, the breathable interface systems 100, 200, 500, and 600 may further include the interface 402 as shown in FIG. 4 for facilitating the fluid communication and flow between the first pad section 102 and/or fabric layer 106 and the reduced pressure conduit 112. In yet another illustrative embodiment, the reduced pressure conduit 112 may not be in direct contact with the first pad section 102 and/or fabric layer 106, but may otherwise be in fluid communication with the first pad section 102 and/or fabric layer 106.

In one illustrative embodiment, the side 120 of the second pad section 104 extends between the top surface 124 and a bottom surface 128 of the second pad section 104. The bottom surface 128 of the second pad section 104 may have a surface area that may cover substantially all or a portion of the top surface 132 of the end 116 of the applicator 110. Additionally, the side 122 of the first pad section 102 extends between the top surface 130 and the bottom surface 126 of the first pad section 102. The bottom surface 126 of the first pad section 102 may have a surface area that may cover substantially all or a portion of the end 114 of the top surface 132 of the applicator 110.

The applicator 110 may be any size desirable to adequately provide effective covering and functionality to a tissue site as described herein. In one aspect, the applicator 110 includes a bottom surface 134 that may preferably contact the tissue site. The end 116 of the applicator 110 may have a surface area of a different shape than the end 114 of the applicator 110. For example, the surface area of the end 116 as shown in FIG. 1 shows a surface area of a substantially circular shape. Nevertheless, the shape of the end 116 of the applicator 110 may any desirable shape, symmetric, asymmetric, or otherwise, to provide the covering of a tissue site and functionality as herein described. In one illustrative embodiment, the end 114 of the applicator 110 may have a surface area that approximates a rectangular shape; however, the end 114 of the applicator 110 may also be any desirable shape, symmetric, asymmetric, or otherwise, to provide the covering and functionality as herein described.

Preferably, the bottom surface 136 of the drape 108 covers and secures the first pad section 102, fabric layer 106, and second pad section 104 to the top surface 132 of the applicator 110. In one aspect, the applicator 110 and drape 108 are sealed together substantially around the perimeter or periphery of their respective shapes. Preferably, the applicator 110 and drape 108 isolate the tissue site from its surrounding environment and maintain a reduced pressure at the tissue site when reduced pressure is applied as described herein. The applicator 110 may be secured to drape 108 with any suitable bonding agent, such as an acrylic adhesive or hydrogel. In addition, the applicator 110 may be joined to the drape 108 by other commonly known means, such as bonding, adhesives, welding, fastening, and sintering, for example. Typically, a hydrogel or other tissue-friendly bonding agent may be applied to the tissue side or bottom surface 134 of the applicator 110, which is then placed into the tissue site or in contact with the perimeter of the tissue site to secure the dressing to the tissue site.

In an illustrative embodiment, the first pad section 102 and second pad section 104 may be a material known in the art to be suitable for reduced pressure tissue treatment, the size and shape of which may be varied to accommodate tissue sites of various size and shape as described herein. Preferably, the first pad section 102 and second pad section 104 include a plurality of flow channels or pathways to facilitate the distribution of reduced pressure or fluids to or from the tissue site. In one illustrative embodiment, the first pad section 102 and second pad section 104 are porous foam that includes interconnected cells or pores that act as flow channels. In addition to the above, the first pad section 102 and second pad section 104 may be a material such as an open cell, reticulated foam that is formed from a range of polymers, including without limitation polyurethane, polyolefin, vinyl acetate, polyvinyl alcohol, and their copolymers. Additionally, the first and second pad section 102, 104 may be woven or non-woven materials, including 3-dimensional fabric structures. The pads may also be made from a sintered polymer, including materials such as sintered polyolefin, ethylene vinyl acetate, and fluoropolymer. The first pad section 102 and second pad section 104 may also be any other type of open-cell, reticulated foam, such as GranuFoam® and Whitefoam™ that are manufactured by Kinetic Concepts, Inc. of San Antonio, Tex. If open-cell foam is used, the porosity may vary, but is preferably about 400 to 600 microns. Alternatively, gauze or any other material suited to a particular biological application may be used to construct first pad section 102 and second pad section 104. In a certain illustrative embodiment, first pad section 102 and second pad section 104 may be constructed as a single, unitary pad. In another illustrative embodiment, first pad section 102 and second pad section 104 may be a multi-component or multi-layered pad section. Preferably, the thicknesses of the first pad section 102 and second pad section 104 is from about 1 mm to about 50 mm, and in one implementation from about 5 mm to about 20 mm, although any thicknesses may be used.

In an illustrative embodiment, the fabric layer 106 may be a woven or non-woven fabric material known in the art, the size and shape of which may be varied to accommodate tissue sites of various size and shape as described herein. It may be constructed from any fiber material that maintains its structural integrity when exposed to fluids, such as polyamide, polyolefin, nylon, polyester, a polyamide coated with polyurethane, any polymeric mesh, a non-woven (air layed) melt blown polymer, or flexible sintered polymer. The fabric layer 106 may also be a fabric covered with adhesive or hydrogel to facilitate bonding to the tissue site, where the fabric layer 106 extends beyond the applicator 110. The material may be woven together to form a layer of appropriate dimensions, or it may be any type of open cell mesh construction of appropriate dimensions. As illustrated in FIG. 1, the fabric layer 106 may also be folded and include stitching 140 to provide additional channels and structural support. A folded fabric layer may be stitched lengthwise down the middle, as depicted in FIG. 2, around the edges, or any combination thereof. As an alternative to stitching, a folded fabric layer may be secured with an acrylic adhesive or any other suitable bonding agent. The fabric layer 106 may also include several overlapping layers joined together by any known means. Preferably, the thicknesses of the fabric layer 106 is from about 1 mm to about 50 mm, and more preferably about 5 mm to about 20 mm, although any thicknesses may be used.

The drape 108 may be a flexible material having a sufficiently high moisture vapor transmission rate ("MTVR") to preclude tissue maceration, typically greater than 600 mg/m$^2$/day. In one aspect, plastics and thermoplastics are an example of suitable materials for the drape 108. And like the drape 108, the applicator 110 generally is constructed from any flexible material having a sufficiently high MTVR to preclude maceration of the tissue site, such as plastics and thermoplastics.

The reduced pressure conduit 112 may represent any conduit tubing, line, or path through which a gas, liquid, gel, or other fluid may be carried, and may have more than one internal lumen. While the reduced pressure conduit 112 may be inflexible, it is preferred that it be flexible enough for ease of use and comfort for a patient. The reduced pressure conduit is configured for connection to a reduced pressure source to provide delivery of reduced pressure.

In an illustrative embodiment, the breathable interface systems 100, 200, 500, and 600 may be lightweight, low-profile interface systems for low-severity, small tissue sites, but the principles are readily extendable by a person of ordinary skill in the art to larger, more extensive tissue sites, as well as numerous other types of tissue treatments.

Referring again to FIGS. 1-6, the aperture 302 is placed over a tissue site and the reduced pressure source 704 delivers a reduced pressure through the reduced pressure conduit 112 to the breathable interface systems 100, 200, 500, and 600. The aperture 302 may be a single aperture as shown, or any number or plurality of holes, openings, apertures, slits, or the like desirable for providing distribution of reduced pressure and fluid transmission between the tissue site and the first pad section 102, second pad section 104, and fabric layer 106. As described above, the first pad section 102 and second pad section 104 may include pathways or channels that permit the reduced pressure to be distributed throughout the breathable interface systems 100, 200, 500, and 600, and that permit fluids to be removed from a tissue site through the aperture 302. The weave or mesh structure of the fabric layer 106 provides additional fluid pathways that are less susceptible to collapsing under compressive loads that may be applied to the breathable interface systems 100, 200, 500, and 600, such as those encountered when a patient rolls in bed or otherwise moves causing compression of the dressing. The additional fluid pathways also reduce the time required to distribute reduced pressure to a tissue site. As detailed below, testing has shown that pressure changes by a reduced pressure source are communicated to the tissue site much more quickly with a dressing configured like that of the breathable interface systems 100, 200, 500, and 600.

Figure 7:
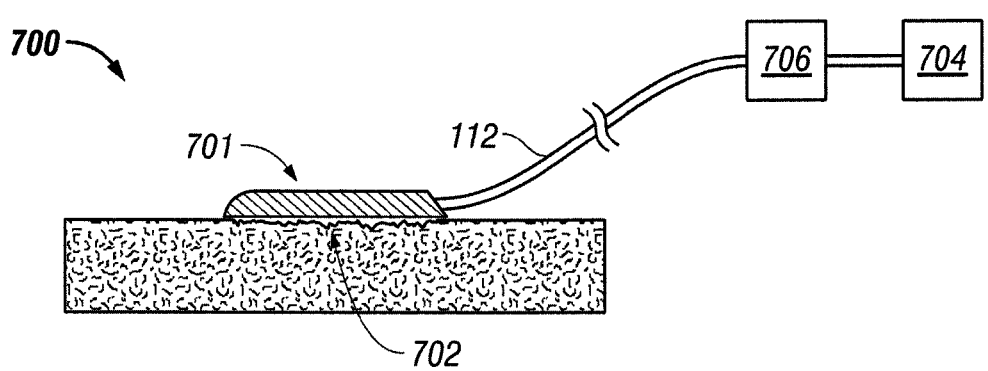
FIG. 7 is a schematic diagram of a reduced pressure tissue treatment system having a breathable interface system according to an illustrative embodiment of the invention.

Referring to FIG. 7, an illustrative embodiment of a reduced pressure tissue treatment system 700 incorporating the novel features of the breathable interface system is shown. The reduced pressure tissue treatment system 700 includes a breathable interface system 701 similar to the other breathable interface system described herein, which is applied to a tissue site 702 for treatment. Breathable interface system 100 is fluidly connected to a reduced pressure source 704 by a reduced pressure conduit 112. In certain embodiments, the reduced pressure tissue treatment system 700 may also include a canister 706 for collecting fluid and other non-gaseous exudates extracted from the tissue site 702.

Figure 8:
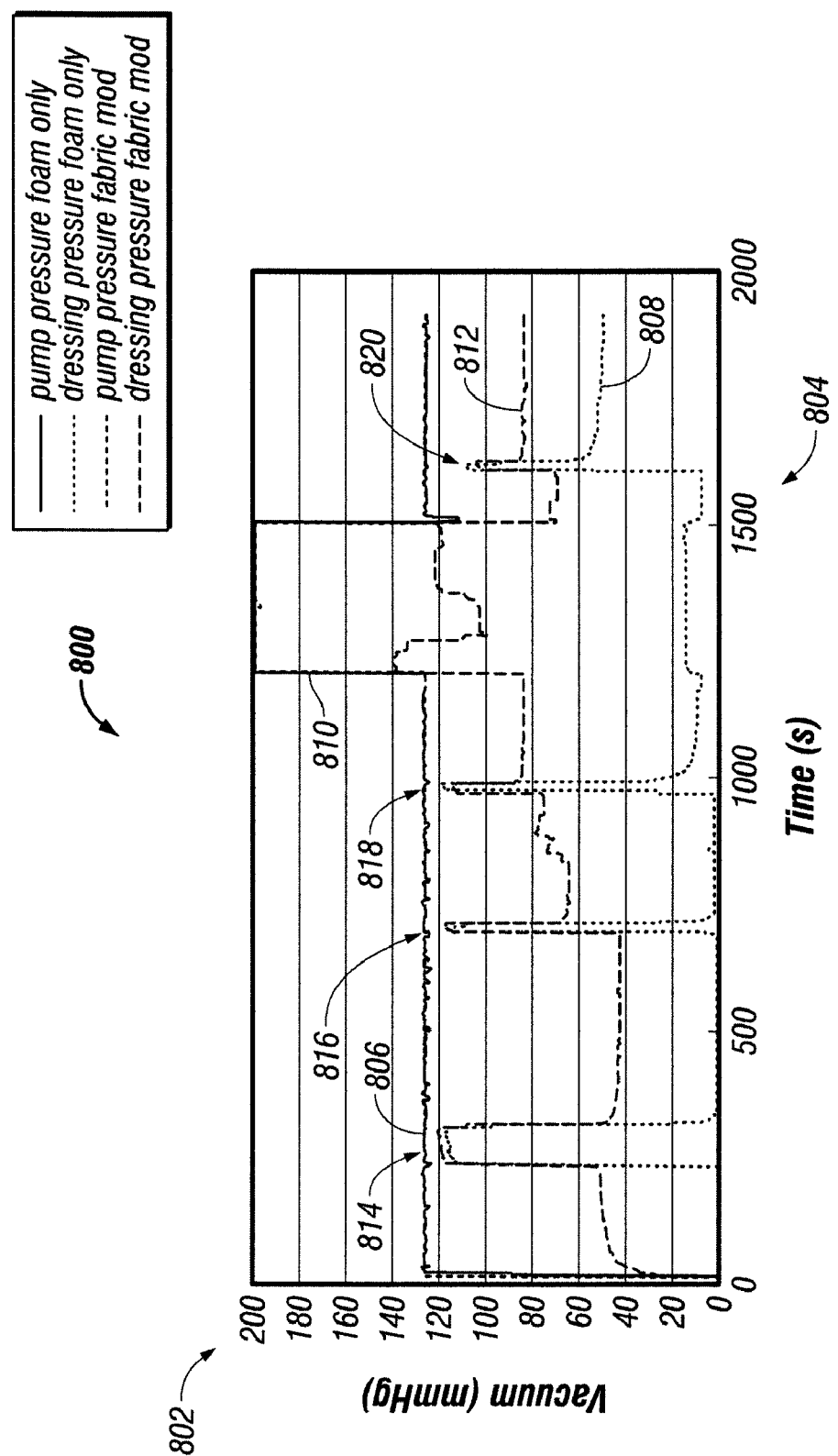
FIG. 8 is a chart that compares the results of pressure transmission experiments on a conventional dressing and a breathable interface system according to an illustrative embodiment of the present invention.

Referring to FIG. 8, a chart that compares the results of pressure transmission tests on a conventional dressing and a breathable interface system 100 as substantially described above is shown. In the tests, reduced pressure was applied to and water was pumped through each breathable interface system 100 while the breathable interface system 100 was subjected to a range of compressive forces. Pressure measurements were taken on both sides of the compressive forces to determine the performance of each specimen. The results, as shown in FIG. 8, demonstrate that a breathable interface system 100 as described above enables pressure communication across the compressive load to a much greater extent that a conventional dressing.

The flow of water was set to approximately 20 mls/hr and a compressive force from approximately 0 N to about 500-930 N was applied to the conventional dressing and the breathable interface system 100. The y-axis 802 represents the amount of reduced pressure or vacuum measured at either the pump or the dressing/breathable interface system 100. The x-axis 804 represents the duration of time expired from the start of the tests. Line 806 represents the magnitude of the reduced pressure at the pump for the conventional dressing and the line 808 represents the magnitude of the reduced pressure at the opposite side of the dressing. As can be seen from FIG. 8, a compressive force of approximately 900 N was applied to the conventional dressing and the amount of measurable reduced pressure was approximately 0 mm Hg. at the dressing, as shown by line 808. At the start of event 814, the compressive force was released, thus the amount of measurable reduced pressure at the dressing increased to approximately 120 mm Hg. At the end of event 814, a compressive force was applied at a magnitude of 525 N and the amount of measurable reduced pressure dropped back to approximately 0 mm Hg. During this same event, the measurable reduced pressure at the pump side of the dressing, as shown by line 806, stayed at approximately 125 mm Hg. This shows that with a conventional dressing under compressive force, the amount of reduced pressure through the dressing is approximately 0 mm Hg. Similarly, at events 816, 818, and 820, compressive forces were released and reapplied at approximately 250 N. It can be seen from FIG. 8, that essentially the same results followed. Namely, as soon as a compressive force was applied, the measurable amount of reduced pressure through the conventional dressing dropped to 0 mm Hg, or near 0 mm Hg.

Conversely, line 810 represents the magnitude of the reduced pressure at the pump for the breathable interface system 100 and the line 812 represents the magnitude of the reduced pressure at the opposite side of the dressing. As described above, a compressive force of approximately 900 N was applied to the conventional dressing and the amount of measurable reduced pressure was approximately 50 mm Hg at the dressing, as shown by line 812. At the start of event 814, the compressive force was released, thus the amount of measurable reduced pressure at the dressing increased to approximately 120 mm Hg. At the end of event 814, a compressive force was applied at a magnitude of 525 N and the amount of measurable reduced pressure was reduced to approximately 50 mm Hg. During this same event, the measurable reduced pressure at the pump side of the dressing, as shown by line 810, stayed at approximately 125 mm Hg. This shows that with a breathable interface system 100 under compressive force, the amount of reduced pressure is still substantial. Similarly, at events 816, 818, and 820, compressive forces were released and reapplied at approximately 250 N. It can be seen from FIG. 8, that even better results followed. Namely, as soon as a compressive force of approximately 250 N was applied, the measurable amount of reduced pressure through the conventional dressing increased to between approximately 70 mm Hg and 100 mm Hg.

Figure 9:
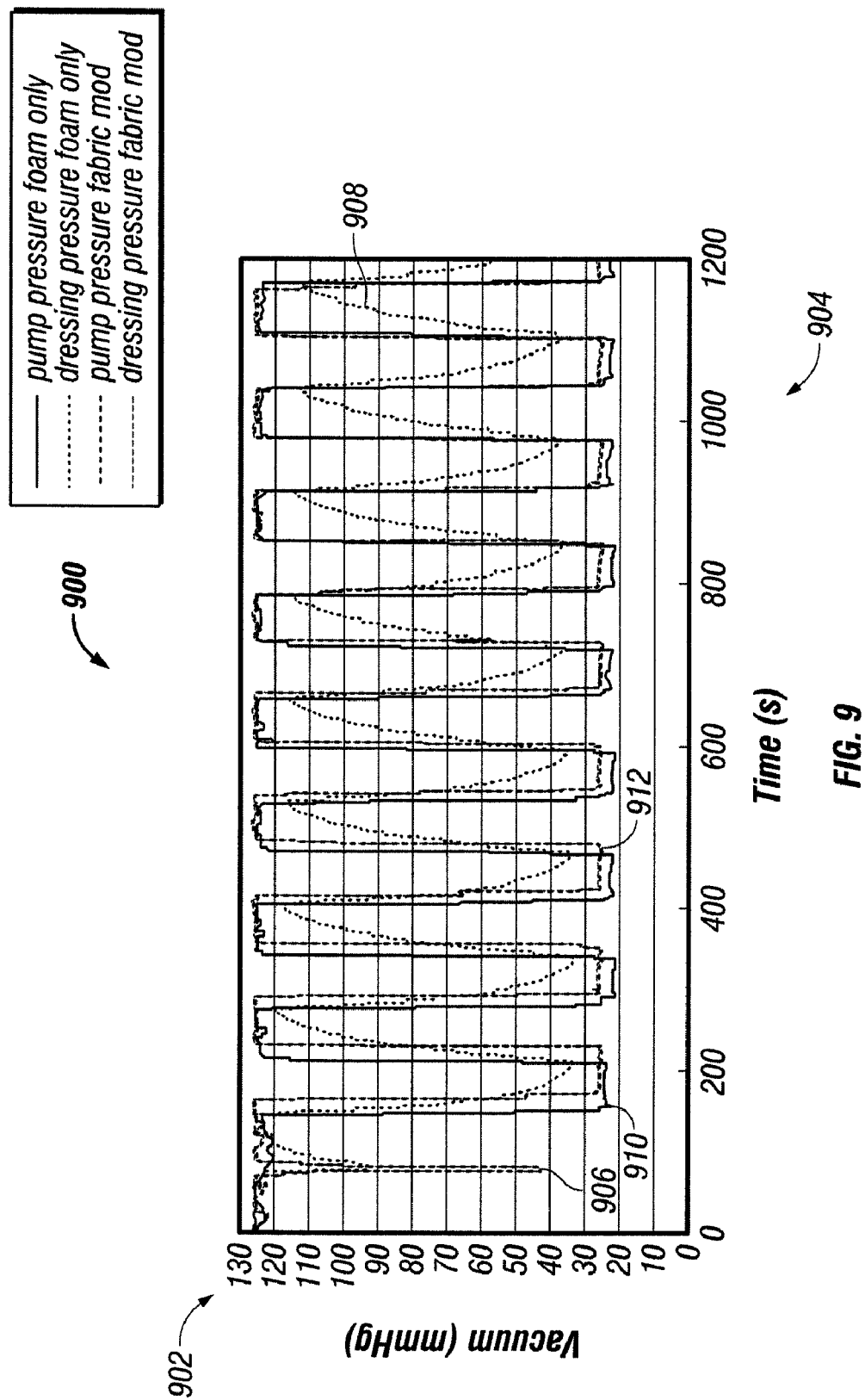
FIG. 9 is a chart that compares response times when subjected to intermittent application of reduced pressure under dry conditions of a conventional dressing and a breathable interface system according to an illustrative embodiment of the present invention.

Referring to FIG. 9, another chart is shown that compares response times of a conventional dressing and a breathable interface system 100 as substantially described above in FIG. 8 when subjected to intermittent application of reduced pressure under dry conditions. The response times illustrated in FIG. 9 demonstrate that a conventional dressing responds much more slowly than the breathable interface system 100 described above when subjected to these conditions.

Pressure measurements were taken on both sides of the compressive forces to determine the response times of a conventional dressing compared with the breathable interface system 100 described above. The results, as shown in FIG. 9, demonstrate that a breathable interface system 100 as described above enables faster response times to the intermittent application and release of reduced pressure. The y-axis 902 represents the amount of reduced pressure or vacuum measured at either the pump or the dressing/breathable interface system 100. The x-axis 904 represents the duration of time expired from the start of the tests. Line 906 represents the magnitude of the reduced pressure measured at the pump for the conventional dressing and the line 908 represents the magnitude of the reduced pressure at the opposite side of the dressing. Line 910 represents the magnitude of the reduced pressure measured at the pump for the breathable interface system 100 and the line 912 represents the magnitude of the reduced pressure measured at the opposite side of the breathable interface system 100.

As can be seen from FIG. 9, a reduced pressure is cycled on and off between approximately 0 mm Hg and 125 mm Hg. The lines 906 and 910 fairly closely match each other showing that there is little difference of measurable reduced pressure during the tests at the pump side of the dressing/breathable interface system 100 during the cycling of the reduced pressure. At the other side of the dressing, line 908 shows a lag time in achieving the applied reduced pressure at the conventional dressing. This can be seen as line 908 has an arc to its shape representing the gradual building of reduced pressure before it attains full reduced pressure. Conversely, line 912 shows sharp transitions when the reduced pressure is cycled on and off, thus representing that the breathable interface system 100 provides for improved fluid transmission and response to reduced pressure than conventional dressings.

It should be apparent from the foregoing that an invention having significant advantages has been provided. While the invention is shown in only a few of its forms, it is not just limited but is susceptible to various changes and modifications without departing from the spirit thereof.

We claim:

1. A reduced pressure tissue treatment system comprising:
   an applicator having an aperture;
   a first pad section;
   a second pad section substantially covering the aperture and positioned substantially adjacent the first pad section;
   a fabric layer located at least partially between the second pad section and a drape, the fabric layer including a woven or non-woven fabric made from a fiber material;
   the drape substantially covering the first pad section, the second pad section, the fabric layer, and the applicator; and
   a reduced pressure source in fluid communication with at least one of the first pad section and the fabric layer for providing reduced pressure to the aperture.

2. The reduced pressure tissue treatment system of claim 1 further comprising a canister fluidly connected between the reduced pressure source and the at least one of the first pad section and the fabric layer.

3. The reduced pressure tissue treatment system of claim 1, wherein the fabric layer is located at least partially between the first pad section and the applicator.

4. The reduced pressure tissue treatment system of claim 1 further comprising an interface located between the reduced pressure source and the at least one of the first pad section and the fabric layer.

5. The reduced pressure tissue treatment system of claim 1, wherein the first pad section and the second pad section are selected from the group consisting of open-cell reticulated foam, sintered polymers, ethylene vinyl acetate, fluoropolymers, polyurethane, polyolefin, vinyl acetate, polyvinyl alcohol, and their copolymers.

6. The reduced pressure tissue treatment system of claim 1, wherein the fabric layer is selected from the group consisting of polyamide, nylon, polyamide coated with polyurethane, polymeric meshes, non-woven melt blown polymers, and flexible sintered polymers.

7. The reduced pressure tissue treatment system of claim 1, wherein the first pad section, the second pad section, and the fabric layer have a thickness of from about 5 mm to about 20 mm.

8. The reduced pressure tissue treatment system of claim 1, wherein the fabric layer includes several overlapping layers joined together.

9. A reduced pressure tissue treatment system comprising:
   an applicator having an aperture;
   a first pad section;
   a second pad section substantially covering the aperture and positioned substantially adjacent to the first pad section;
   a fabric layer located at least partially between the first pad section and the applicator, the fabric layer further being located at least partially between the second pad section and the applicator;
   a drape substantially covering the first pad section, the second pad section, the fabric layer, and the applicator; and
   a reduced pressure source in fluid communication with at least one of the first pad section and the fabric layer for providing reduced pressure to the aperture.

10. The reduced pressure tissue treatment system of claim 9 further comprising a canister fluidly connected between the reduced pressure source and the at least one of the first pad section and the fabric layer.

11. The reduced pressure tissue treatment system of claim 9 further comprising an interface located between the reduced pressure source and the at least one of the first pad section and the fabric layer.

12. The reduced pressure tissue treatment system for claim 9, wherein the first pad section and the second pad section are selected from the group consisting of open-cell reticulated foam, sintered polymers, ethylene vinyl acetate, fluoropolymers, polyurethane, polyolefin, vinyl acetate, polyvinyl alcohol, and their copolymers.

13. The reduced pressure tissue treatment system of claim 9, wherein the fabric layer is selected from the group consisting of woven fabric, non-woven fabric, polyamide, nylon, polyamide coated with polyurethane, polymeric meshes, non-woven melt blown polymers, and flexible sintered polymers.

14. The reduced pressure tissue treatment system of claim 9, wherein the first pad section, the second pad section, and the fabric layer have a thickness from about 5 mm to about 20 mm.

15. The reduced pressure tissue treatment system of claim 9, wherein the fabric layer includes several overlapping layers joined together.

16. A reduced pressure tissue treatment system comprising:
   an applicator having an aperture;
   a first pad section;
   a second pad section substantially covering the aperture and positioned substantially adjacent to the first pad section;
   a fabric layer located at least partially between the first pad section and a drape, the fabric layer further being located at least partially between the second pad section and the drape;
   the drape substantially covering the first pad section, the second pad section, the fabric layer, and the applicator; and
   a reduced pressure source in fluid communication with at least one of the first pad section and the fabric layer for providing reduced pressure to the aperture.

17. The reduced pressure tissue treatment system of claim 16 further comprising a canister fluidly connected between the reduced pressure source and the at least one of the first pad section and the fabric layer.

18. The reduced pressure tissue treatment system of claim 16 further comprising an interface located between the reduced pressure source and the at least one of the first pad section and fabric layer.

19. The reduced pressure tissue treatment system of claim 16, wherein the first pad section and the second pad section are selected from the group consisting of open-cell reticulated foam, sintered polymers, ethylene vinyl acetate, fluoropolymers, polyurethane, polyolefin, vinyl acetate, polyvinyl alcohol, and their copolymers.

20. The reduced pressure tissue treatment system of claim 16, wherein the fabric layer is selected from the group consisting of woven fabric, non-woven fabric, polyamide, nylon, polyamide coated with polyurethane, polymeric meshes, non-woven melt blown polymers, and flexible sintered polymers.

21. The reduced pressure tissue treatment system of claim 16, wherein the first pad section, the second pad section, and the fabric layer have a thickness of from about 5 mm to about 20 mm.

22. The reduced pressure tissue treatment system of claim 16, wherein the fabric layer includes several overlapping layers joined together.

* * * * *